US00PP12615P2

(12) United States Plant Patent
Pouw

(10) Patent No.: US PP12,615 P2
(45) Date of Patent: May 7, 2002

(54) HYBRID TEA ROSE PLANT NAMED 'PANAMARIL'

(75) Inventor: Anton A. Pouw, Kwakel (NL)

(73) Assignee: Panorama Roses N.V., Neerlandesas (AN)

( * ) Notice: Subject to any disclaimer, the term of this patent is extended or adjusted under 35 U.S.C. 154(b) by 0 days.

(21) Appl. No.: 09/523,879

(22) Filed: Mar. 13, 2000

(51) Int. Cl.[7] ..... A01H 5/00
(52) U.S. Cl. ..... Plt./134
(58) Field of Search ..... Plt./134, 133, 130

(56) References Cited

PUBLICATIONS

UPOV–ROM GTITM Computer Database 2001/01, Feb. 6, 2001, GTI Jouve Retrieval Software, Citation for Rosa 'Panamaril'.*

* cited by examiner

*Primary Examiner*—Bruce R. Campell
*Assistant Examiner*—June Hwu
(74) *Attorney, Agent, or Firm*—Christie, Parker & Hale, LLP

(57) ABSTRACT

A new variety of hybrid tea rose plant producing yellow flowers of good form.

2 Drawing Sheets

BACKGROUND OF THE INVENTION

The present invention relates to a new and distant variety of rose plant of the hybrid tea rose class which was created by crossing undistributed, unnamed and unpatented seedlings as seed and pollen parents in The Netherlands. The varietal denomination of the new variety is 'Panamaril'.

SUMMARY OF THE INVENTION

Among the novel characteristics possessed by this new variety which distinguish it from its parent and all other varieties of which I am aware are its attractive yellow flowers.

Asexual reproduction by budding of the new variety as performed in The Netherlands shows that the foregoing and other distinguishing characteristics come true to form and are established and transmitted through succeeding propagations. The new variety has been reproduced through propagation by cuttings, grafting, budding and micropropagation.

BRIEF DESCRIPTION OF ILLUSTRATION

The accompanying two illustrations show typical specimens of the vegetative growth and flowers of the new variety in different stages of development, and as a cut flower, depicted in color as nearly true as it is reasonably possible to make the same in a color illustration of this character.

DESCRIPTION OF THE NEW VARIETY

The following is a detailed description of 9-month old plants of the new variety, with color terminology in accordance with The Royal Horticultural Society Colour Chart (R.H.S.C.C.) and horticultural terminology in accordance with standard terminology used in UPOV-approved horticultural guideline. The terminology used in color descriptions herein refers to plate numbers in the aforementioned color chart. Phenotypic expression may vary depending upon growing conditions under different climate, soil, and cultivation conditions.

Parentage: Seed and pollen parents are seedlings.
Class: Hybrid Tea.

As can be seen in the accompanying detail illustration there is shown a new shoot, 1; compound three, five and seven leaflet leaves, 2, 3 and 4, respectively; a stem, 5; buds, 6 and 7; a flower, 8, about one-third open to one-half open and a flower, 9, more fully open. Also shown are flower stems 10, 11 and 12, with reproductive organs displayed.

COMPARISON WITH PARENTS

The female parent produces yellow roses, and the male parent produces yellow ochre flowers.

The following further horticultural description is based on observations made of specimens grown under glass in The Netherlands.

FLOWER

A. Blooming habit: Recurrent.
B. Bud:
- *Size.*—Large, about 50 mm long×32 mm wide.
- *Form.*—Ovate.
- *Color.*—When sepals first divide: near 13A (plus near 138b).
- *Sepals.*—Can be divided into two types, being with protrudes and without protrudes at each side. Each flower is having 2 sepals without protrudes at the side, dimensions about 30×10 mm. These sepals are bulb-shaped towards a point. At this point there is a protrude of around 10 mm long and 2 mm wide. The other 3 sepals do have 3 to 4 protrudes at the side (often 1 sepal with protrudes at 1 side), the dimensions 5–10 mm. At the interior the sepals are fluffy, color near 138B. At the under side they are smooth, color near 144A. Color of protrudes top surface near 139A and lower surface near 144A.
- *Peduncle.*—Length about 8.5 cm; smooth; color near 143C.

C. Bloom:
- *Size.*—Average size when fully open — about 11 cm.

*Borne.*—Singly.

*Form.*—Side view of upper part fully opened is flattened convex, side view of lower part fully opened is flattened convex.

*Petalage.*—About 22.

*Color.*—Outer Petals: Top surface, near 9A to 9C; Under surface, near 9C to 9D. Inner Petals: Top surface near 12A; under surface near 13B. Base: Top surface near 9A, under surface near 9C.

*General tonality from a distance.*—Yellow. Outer Petals: Top surface, near 9C to 9D; under surface, near 4D. Inner Petals: Top surface near 9Bto 9C under surface about 9C to 9D. Base: Top surface near 9A, under surface near 9C.

*Color change as bloom matures.*—Lightens somewhat. General Tonality at a distance: Light yellow, near 9C to 9D.

D. Petals:

*Appearance.*—Velvety.

*Form.*—Wide, round; undulation of margin is medium.

*Arrangement.*—Imbricated, petal size about 50–63 mm length×50–68 mm wide, surface texture is smooth, petals are reflexed, at the upper surface there is a small little point, at the under surface somewhat widening connecting point of around 3 mm.

*Petaloids.*—About 4, top surface near 12A, under surface near 13B, length about 15–35 mm, width about 5–30 mm, surface texture wrinkled.

*Persistence.*—Persistent.

*Lasting quality on plant and after cutting.*—Vase life about 14 days, on the plant about 21 days.

PLANT

A. Form: Upright.

B. Growth: Vigorous.

*Height attained.*—About 1.60 m.

*Spread.*—About 0.6–0.7 m.

C. Foliage: Compound 3, 5 and 7 leaflets.

*Size.*—About 13 cm to 16 cm, top leaflet size about 5 to 9 cm in length and about 4 to 5.5 cm in width, other leaflets about 3.5 to 6.5 cm in length and about 1.5 to 4.5 cm in width, apex wedge shaped, base shape is obtuse.

*Quantity.*—About 15 leafs per stem.

*Color.*—New foliage: Upper side near 143B to 143C and near 187A — Under side near 143C and near 187A to 187B. Old foliage: Upper near 139A — Under side near 137B.

*Shape.*—Ovate.

*Texture.*—Upper side, veins are sunken; underside, veins are swollen (rise above the surface).

*Edge.*—Serrated.

*Serration.*—Serrate.

*Petiole.*—Texture at the top surface is somewhat gully shaped, under surface is round and smooth, length about 3 mm. Color: Upperside: Near 187A to 187B. Underside: Near 137C.

*Stipules.*—Upperside near 137A; middle near 138B; Underside near 138A.

*Rachis.*—About 6 to 10 cm, at the under surface there are 2 prickles, top surface near 187B, under surface near 137C.

*Resistance to disease.*—Susceptible to powdered mildew, rust and blackspot.

D. Wood.

*New shoots.*—Color: Near 137C to 137D. Bark: Smooth.

*Old wood.*—Color: Green Group near 137D. Bark: Smooth.

*Flower stem length from last cut.*—Near 90 cm.

E. Thorns: Upper part of stem is free of thorns, remainder of stem has about 2 to 4 thorns per internode.

*Form.*—Upper side straight; lower side concave.

*Medium.*—Medium, about 7 mm length.

*Color.*—Immature thorns near 183A, mature thorns near 176A to 176B.

*Position.*—Irregular.

*Prickles.*—Some.

F. Winter hardiness: Not known, glasshouse variety.

G. Flower production: About 140 stems/$m^2$/year.

REPRODUCTIVE ORGANS

A. Stamens, filaments and anthers:

*Arrangement.*—Regularly arranged around pistil.

*Color.*—Stamens: Near 17B. Filament: Near 13B. Anthers: Near 17B. Styles: Near 4D and near 43B. Stigmas: Near 5C. Hip: Not observed.

*Length.*—Filament: 5 to 10 mm. Anther: About 3 mm. Style: 6 to 8 mm.

*Number.*—Stamens: About 160. Pistils: About 120.

B. Pollen: Color — yellow brown.

C. Styles: Uneven length.

D. Stigmas: Color — pink red.

E. Hips:

*Shape.*—Pitcher shaped.

*Size.*—2.5×2 cm.

*Color.*—Orange.

*Seeds.*—Protrude somewhat.

F. Receptacle and calyx: Receptacle color outside near 143C, shape of calyx is round about 10 mm width and around 8 mm length, outside is smooth, interior is covered with white woolly fluff.

G. Anthocyanin:

*Petiole.*—Somewhat near 177A.

*Rachis.*—None.

*Stem.*—Somewhat near 177A.

*Peduncle.*—None.

*Sepals.*—None.

What is claimed is:

1. A new and distinct rose plant of the hybrid tea variety substantially as shown and described.

* * * * *

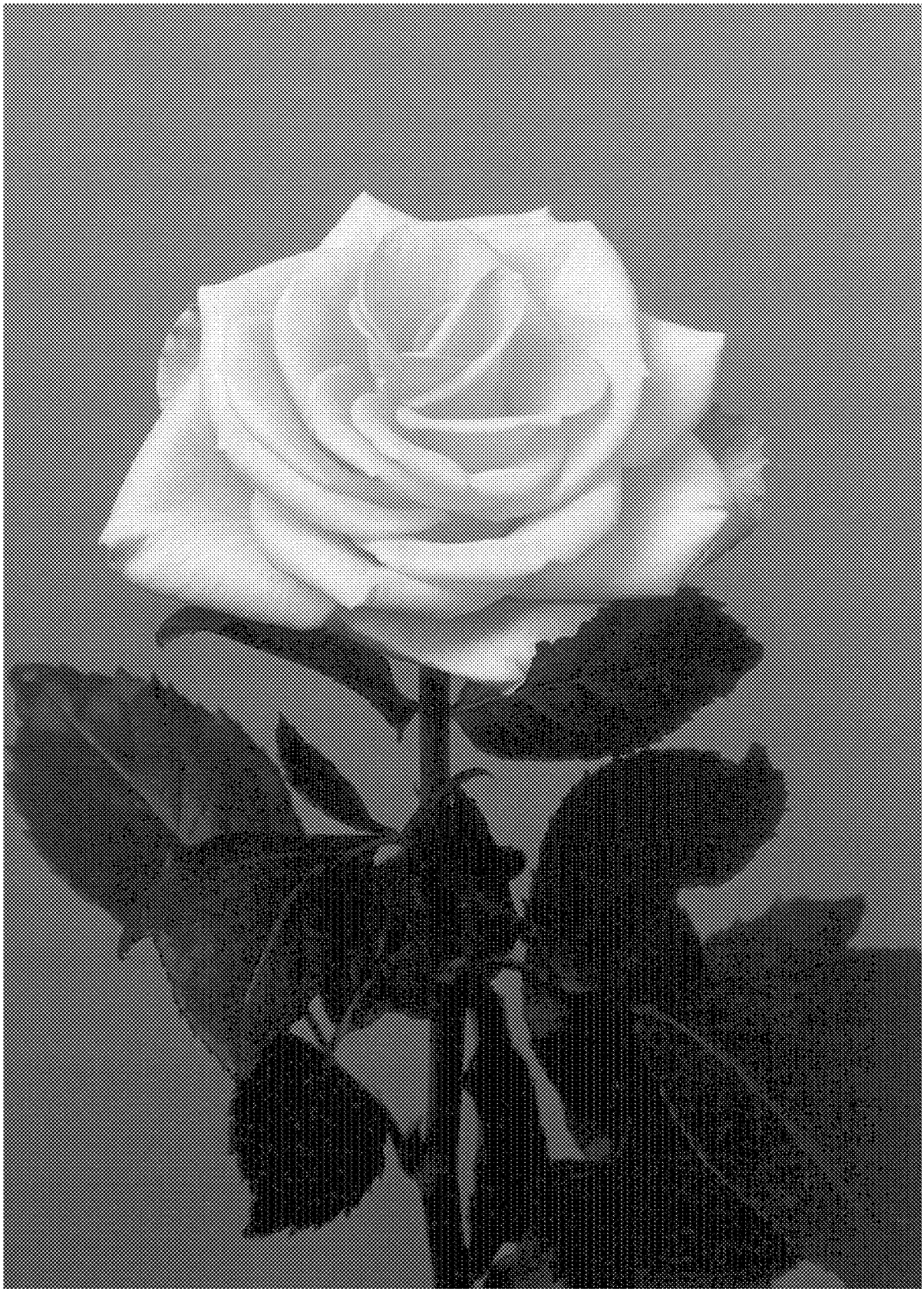

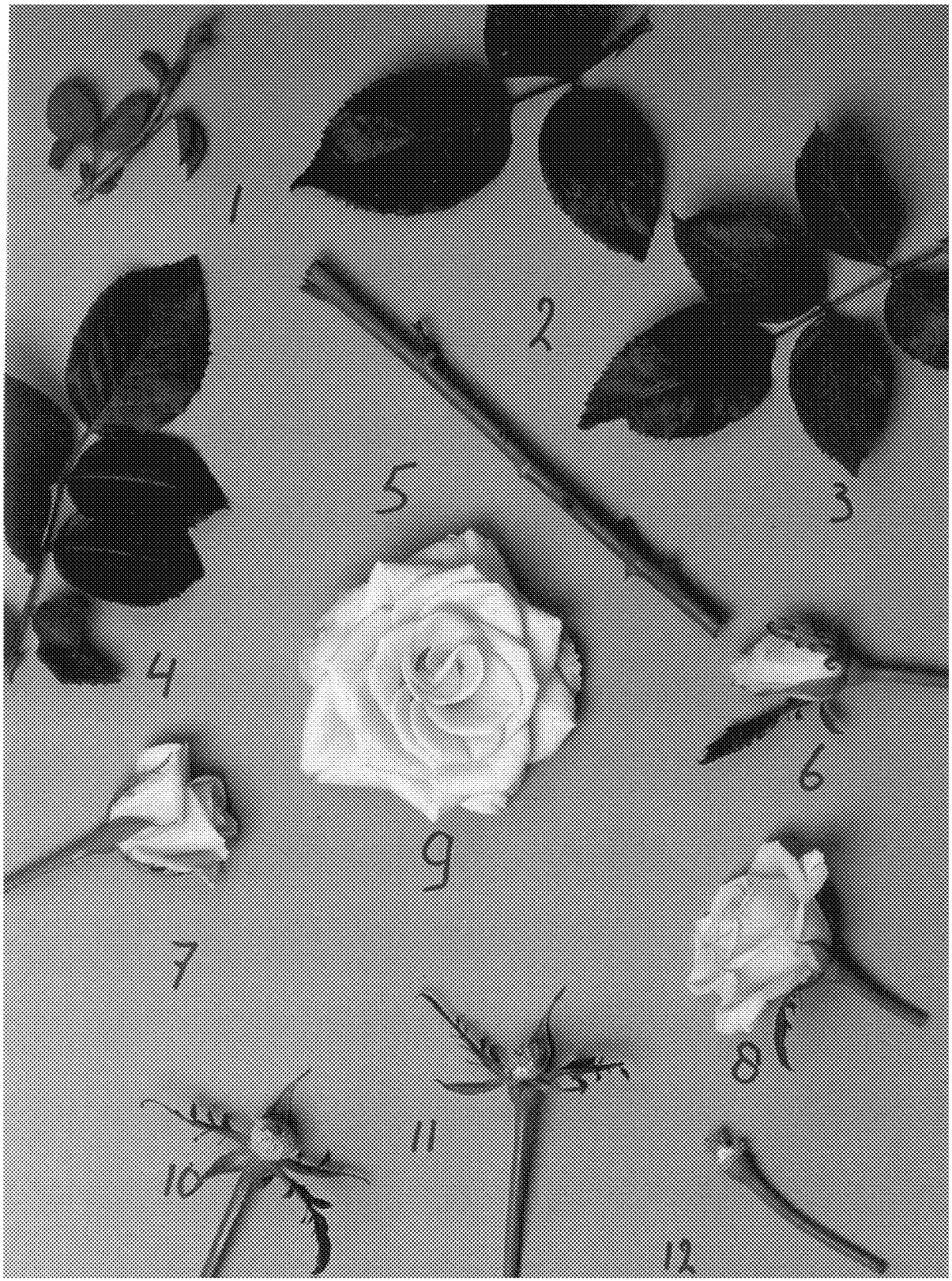
1
2
3
4
5
6
7
8
9
10
11
12